United States Patent [19]

Verdooner et al.

[11] Patent Number: 5,220,360
[45] Date of Patent: Jun. 15, 1993

[54] APPARATUS AND METHOD FOR TOPOGRAPHICAL ANALYSIS OF THE RETINA

[75] Inventors: Steven R. Verdooner, Sacramento; Patricia C. Meade, Esparto; Dennis J. Makes, Sacramento, all of Calif.

[73] Assignee: Ophthalmic Imaging Systems, Inc., Sacramento, Calif.

[21] Appl. No.: 602,628

[22] Filed: Oct. 24, 1990

[51] Int. Cl.⁵ .............................................. A61B 3/10
[52] U.S. Cl. ..................................... 351/212; 351/247
[58] Field of Search ....................... 351/212, 247, 246; 356/376

[56] References Cited

U.S. PATENT DOCUMENTS

| | | |
|---|---|---|
| 4,423,931 | 1/1984 | Shapiro . |
| 4,579,430 | 4/1986 | Bille . |
| 4,668,094 | 5/1987 | Matsumoto et al. ................ 356/376 |
| 4,685,140 | 8/1987 | Mount, II . |
| 4,715,703 | 12/1987 | Cornsweet et al. . |
| 4,728,196 | 3/1988 | Gerstorfer . |
| 4,732,466 | 3/1988 | Humphrey . |
| 4,863,260 | 9/1989 | Gersten et al. . |
| 4,867,554 | 9/1989 | Matsumura . |
| 4,900,144 | 2/1990 | Kobayashi . |
| 4,933,756 | 6/1990 | Sekine ..................... 351/206 |
| 4,993,826 | 2/1991 | Yoder .................... 351/212 |
| 4,998,819 | 3/1991 | Labinger et al. . |

FOREIGN PATENT DOCUMENTS 3602995 1/1986 Fed. Rep. of Germany .

OTHER PUBLICATIONS

International Search Report of International Application PCT/US91/07621 (0977-2-PCT) dated Mar. 13, 1992, Applicant: Ophthalmic Imaging Systems, Inc.

Primary Examiner—Rodney B. Bovernick
Attorney, Agent, or Firm—Sixbey, Friedman, Leedom & Ferguson

[57] ABSTRACT

A novel optical subsystem is connected to an analyzing computer. The optical subsystem projects a grid of parallel lines onto a patient's retina, and a video camera in the optical subsystem captures a first retinal image and transmits it to the computer, where the image is digitized for analysis. A second image of the same eye is also captured, with the grid of parallel lines oriented perpendicular to the grid of the first image. The computer stores image data for the patient for a plurality of visits. The computer analyzes the images by forming a skeletonized topographical map of the retinal area of interest. First, a novel one-dimensional line detection algorithm is used to process the images. The line detection algorithm dilates, erodes and restores, Fourier transforms, bandpass filters, thresholds, skeletonizes, line traverses and interpolates the data for each of the two images. The resulting information is normalized to compensate for the effects of the patient's ocular optics. A topographic line map is constructed using the lines detected in the two images and the map is divided into sections for analysis. Using selected landmarks, the computer then registers the map with the topographic maps constructed from images acquired on previous patient visits. Volumetric changes in the topography of the retina as compared to the prior topographies for the patient are calculated, and, with other quantities of interest, are displayed in an easily-interpreted report.

48 Claims, 8 Drawing Sheets

APPARATUS AND METHOD FOR TOPOGRAPHICAL ANALYSIS OF THE RETINA

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

Glaucoma is one of the diseases commonly screened for when a patient visits an optometrist or opthalmologist. In the United States there are approximately 4 million people affected by this disease.

Several diagnostic tests are commonly used for diagnosing glaucoma. These include measurement of intraocular pressure (IOP), visual field checks using a perimeter, and, less frequently, stereo fundus photography for subjective evaluation of the optic nerve head.

The most common screening test is the IOP test, since glaucoma is usually accompanied by an increased intraocular pressure. However, this test, cannot be reliably used to diagnose glaucoma because increased IOP does not necessarily indicate that glaucoma is present. Further, a patient may have so-called "low-IOP glaucoma" in which glaucoma is present without a significantly increased IOP. Thus, the IOP test does not identify all cases of glaucoma. It is used because there is nothing better available at a cost low enough for the majority of opthalmic offices to absorb.

The visual field check using a perimeter can be used to reliably diagnose glaucoma, since loss of visual field eventually occurs as part of the onset of the disease. However, by the time glaucoma can be detected with a perimeter, the disease is well advanced and, although the patient's eyesight can be stabilized at the current level using medication, the visual field already lost is usually not recoverable. Thus, the perimeter check alone, while accurate and inexpensive, does not provide a sufficiently early diagnosis to prevent significant loss of eyesight.

It is well documented in the literature that structural changes in the optic nerve head, which is located at the back of the eye (at the ocular fundus), may be seen by an opthalmologist before the IOP and visual field tests indicate that a patient has glaucoma. As glaucoma progresses, the volume of the optic nerve head increases. In addition, a cupping or excavation may appear in the optic nerve head as the nerve tissue is damaged by the onset of the disease. If these volumetric changes could be detected early enough in a reliable and reproducable manner, then glaucoma could be detected earlier in patients and the loss of eyesight could be prevented. Typically, however, because the IOP and visual field checks are the only widely available glaucoma diagnostic tools, a patient is not diagnosed as having glaucoma until irreversible visual field loss has already occurred. As noted, structural changes to the optic nerve head may presently be clinically identified on a qualitative level, but there is a need for a reliable method for accurately and quantitatively measuring changes in the topography of the optic nerve head.

Of course, other problems may also be detected by measuring volumetric changes in the optic nerve head. For example, brain tumors or fundus tumors can cause the optic disc to decrease in volume.

Several prior art systems have attempted to analyze changes in the optic nerve head for disease diagnosis U.S. Pat. No. 4,423,931 to Shapiro shows a stripe projection accessory for a fundus camera. The apparatus projects a fixed stripe pattern onto the fundus, which is photographed. The specification of this patent indicates that the photographic image produced could be digitized and then analyzed by a computer to identify changes in the structure of the fundus. However, the system disclosed is expensive to produce because it requires projecting a stripe pattern with a large depth of field. Apparently, the modes of analysis referred to by Shapiro could not operate accurately unless the stripe pattern was precisely focussed over the entire optic nerve head. Also, devices of this type suffer repeatability problems since they must be reattached to the fundus camera for each use, producing possible alignment errors that would prevent precise comparison of photos taken at different sittings.

U.S. Pat. No. 4,715,703 to Cornsweet et al. discloses an apparatus for examining an ocular fundus which projects light of variable wavelengths onto the fundus and then uses a stereo camera arrangement to collect data about the fundus. The data is stored digitally and can be overlaid on-screen to show changes in the fundus. An algorithm cross-correlates the stereo images to determine depth information. However, because of the complexity of the optics and multiple camera systems used, such systems are fairly expensive to produce. Further, such systems in practice have not provided the high degree of repeatability and accuracy that is required for clinical use. One significant problem with systems of this type is that any variation in the angle of separation between the stereo image pair will produce a false apparent variation in the depth of the surface being imaged.

In general, the prior art systems that have projected lines or spots on the optic nerve head are limited in that they require sharp focussing of light on the optic nerve head tissue to obtain accurate topographic data. In practice, it is difficult to sharply focus light over the entire optic nerve head since the optic nerve head varies in depth and because the optic nerve head tissue is relatively clear and thus tends to absorb and diffuse the light projected on it. Expensive optical systems were employed in the prior art systems in an attempt to compensate for this characteristic of the retina. However, even complex optics did not provide a solution to the problem. Systems that rely on the focus of lines or laser spots to obtain depth information are inherently flawed in that the persons most at risk for glaucoma tend to have other problems associated with aging eyes. Light from lines or laser spots beamed through an opaque portion of the cornea or lens such as a cateract will be scattered, and accurate depth data will not be obtained if the operation of the system depends on the sharp focus of this light on the optic nerve head. As a result, prior art systems that require accurate focus will not provide accurate optic nerve head depth measurements for the people most at risk.

Additionally, prior-art methods of analysis which require manual examination and comparison of photographic images are time consuming and subjective and are therefore less practical in a clinical environment.

U.S. Pat. No. 4,732,466 to Humphrey discloses a fundus camera which uses a rotating drum which scans an illuminated region across the retina to form an image on a vidicon tube. This system does not perform analysis of the image produced and has moving parts which are less reliable than fixed optoelectronics.

Further systems form ocular images using point light sources such as scanning lasers. Systems of this type are disclosed in U.S. Pat. No. 4,900,144 to Kobayashi, U.S. Pat. No. 4,867,554 to Matsumura, U.S. Pat. No. 4,579,430 to Bille, and U.S. Pat. No. 4,728,196 to Gerstorfer. These systems, like the prior-art line projection systems described previously, are expensive to produce, difficult to adjust to produce repeatable output, and depend on accurate focussing of the laser spots.

U.S. Pat. No. 4,863,260 to Gersten shows a system for topographical modeling of anatomical surfaces, such as the cornea of the eye. The system projects illuminated mires onto the cornea and a video camera transmits the image to a computer. The image is then radially scanned by the computer to provide desired information. The system disclosed is not adapted to compare images or to diagnose diseases such as glaucoma, and is not adapted for determining the topography of internal ocular surfaces such as the optic nerve head.

All of these systems known to the present inventors fail to provide a system for detecting glaucoma and performing other ocular structure diagnosis which is accurate, affordable, and can be used as a regular part of a daily clinical opthalmic practice without an adverse effect on patient throughput. What is needed is a system which has relatively simple and inexpensive optic components and which can collect, in a highly automated and repeatable fashion, accurate topographical information about the retina, and then compare the information collected to stored, previously collected topographic information for the same patient to quantitatively identify changes in the retinal topography. Most importantly, such a system should not rely on accurate focussing of light beams on the retina since characteristics of aging corneas make precise focusing virtually impossible in the patients most at risk for glaucoma.

SUMMARY OF THE INVENTION

Therefore, it is a general object of the present invention to provide a novel and improved apparatus useful in detecting glaucoma and other diseases.

Another general object of the present invention is to provide a novel method for detecting glaucoma and other diseases.

A more specific object of the present invention is to provide an apparatus and method for topographically mapping an internal ocular surface, including projection means for projecting a plurality of parallel lines onto the internal ocular surface in a specified line orientation and with a specified direction of projection, camera means for capturing an image of the internal ocular surface having parallel lines projected thereon, the image being captured at an angle from the direction of projection, and means connected to the camera means for generating digital picture element data representative of the image of the internal ocular surface and for identifying the picture element locations of images of the parallel lines in the image and for generating a topographical map of said internal ocular surface based on imaged curvatures of the projected parallel lines, and comparison means associated with the computer means for retrieving at least one of the types of previously stored data relating to said internal ocular surface and then comparing a first topographical map generated from said previously stored data to a second topographical map generated from more recently obtained data relating to the same internal ocular surface, to identify differences in topography between said first and second maps, for, among other purposes, detecting diseases such as glaucoma.

Another object of the present invention is to provide an apparatus and method for imaging internal ocular surfaces in which an energy projection means and a camera means are contained in a single housing.

It is also an object of the present invention to provide an apparatus and method for imaging internal ocular surfaces in which a video camera is mounted to have a central axis of view of the internal ocular surface, and at least a portion of an energy projection means is movable relative to the axis of view for selectively projecting parallel lines from at least two directions relative to the axis of view.

A further object of the present invention is to provide an apparatus and method for imaging internal ocular surfaces in which a computer uses data gathered from at least two images to form a topographical map.

Yet another object of the present invention is to provide an apparatus and method for imaging internal ocular surfaces in which images are collected with parallel lines projected on the surface in a first direction and also in a second direction different from, and in a preferred embodiment perpendicular to, the first.

It is also an object of the present invention to provide an apparatus and method for imaging internal ocular surfaces in which a line projection apparatus is selectively rotatable about a camera's axis of view so that the lines can be projected in different directions relative to the axis of view.

A further object of the present invention is to provide an apparatus and method for imaging internal ocular surfaces in which a very large number of images can be stored for subsequent recall, and if desired, for comparison to images of the same surfaces taken at other times.

It is another object of the present invention to provide an apparatus and method for imaging internal ocular surfaces in which topographical maps of the surfaces are produced, and the surfaces are divided into defined regions for comparison purposes.

Another object of the present invention is to provide an apparatus and method for imaging internal ocular surfaces which produces a visual report that provides information on topographical differences identified by comparison of one image to a previously taken image.

It is also an object of the present invention to provide an apparatus and method for imaging internal ocular surfaces in which a report includes information on patient intraocular pressures and/or visual field recorded in each case at about the times of capture of image data.

Yet another object of the present invention is to provide an apparatus and method for imaging internal ocular surfaces in which one-dimensional processing algorithms are used to identify the picture element locations of images of projected radiative energy.

A further object of the present invention is to provide an apparatus and method for analyzing internal ocular surfaces in which one-dimensional processing algorithms are executed transversely to the orientation in the image of projected parallel lines.

It is also an object of the present invention to provide an apparatus and method for imaging internal ocular surfaces in which known algorithms are combined in a unique fashion to achieve processing economies and to reduce the quality of the input image data required to achieve accurate analysis.

Another object of the present invention is to provide an apparatus and method for imaging internal ocular surfaces in which Fourier transform and bandpass filter algorithms are used for image processing.

A further object of the present invention is to provide an apparatus and method for imaging internal ocular surfaces in which line skeletonizing algorithms are used for image processing.

It is also an object of the present invention to provide an apparatus and method for imaging internal ocular surfaces which uses a multiple step algorithm made up of individual algorithms to identify the picture element locations of images of parallel lines.

Another object of the present invention is to provide an apparatus and method for imaging internal ocular surfaces in which one or more of dilation algorithms, thresholding algorithms, and erode and restore algorithms are used for image processing.

Yet another object of the present invention is to provide an apparatus and method for imaging internal ocular surfaces that uses a multiple step algorithm made up of individual algorithms to identify the picture element locations of images of parallel lines, including a line traversal algorithm for performing a pixel-by-pixel constrained search to connect associated line segments.

A further broad object of the present invention is to provide an apparatus and method for evaluating changes in internal ocular surfaces which generates a reproducible quantitative output representative of the topography of the surface.

A more specific object of the present invention is to provide an apparatus and method for evaluating changes in internal ocular surfaces which quantitatively measures the relative increase or decrease in the volume of an optic nerve head.

Another broad object of the present invention is to provide an apparatus and method for imaging internal ocular surfaces and detecting changes therein which does not rely on precise focusing of energy waves or particles on the ocular surface.

Another broad object of the present invention is to provide an apparatus and method for imaging internal ocular surfaces which does not require unnatural dilation of the pupils to obtain an image.

Another object of the present invention is to provide a computer system for analyzing internal ocular topography, comprising data input means for receiving internal ocular image data collected from a defined direction and descriptive of an area of interest, the image data including a first set of image data and a second set of image data relating to the same area of interest as the first set of image data and collected at a later time than the first set of image data, and the image data including data representing the images of a plurality of lines projected onto the area of interest at an angle to the image data collection direction, processing means for generating a first set and a second set of topographical data from each of the first and second sets of image data, comparison means for comparing the first and second sets of topographical data and quantitatively identifying topographical changes in the data between the first set and second set, and display means for displaying a report representative of topographical changes identified by the comparison means.

A further object of the present invention is to provide a method for identifying changes in internal ocular topography comprising the steps of (1) obtaining a first set of digital data representing an image of an area of interest, with the area of interest having parallel lines projected thereon through an ocular cornea at the time the image is made, the angle of line projection being different from a direction in which the image was captured, (2) obtaining a second set of digital data representing a later-acquired image of the same area of interest, with the area of interest also having parallel lines projected thereon through the ocular cornea at the time the image is made, the angle of line projection being likewise different from a direction in which the image was acquired; (3) producing first and second sets of line data identifying locations of images of the parallel lines, by executing data filtering algorithms on the first and second sets of data; (5) normalizing the line data as required to compensate for ocular imaging effects; (6) generating a topographical map for each of the first and second sets of data based on imaged curvatures of the projected parallel lines; and (7) comparing the topographical maps for the first and second sets of data to identify changes in volume of the area of interest between the time of obtaining the first set of digital data and the time of obtaining the second set of digital data.

It is another object of the invention to provide a method and apparatus and method for registering two or more sets of image data of a single surface taken at two or more different times relative to the other sets of data to facilitate comparison of the sets of data.

These objects and others are achieved by providing an optical subsystem connected to an analyzing computer. The optical subsystem projects a grid of parallel lines onto a patient's retina, and a video camera in the optical subsystem captures a first retinal image and transmits it to the computer, where the image is digitized for analysis. A second image of the same eye is also captured, with the grid of parallel lines oriented perpendicularly with respect to their orientation in the first image. The computer can store image data for the patient for a large number of visits. The computer analyzes the images by forming a skeletonized topographical map of the retinal area of interest. First, a novel one-dimensional line detection algorithm is used to process the images. The line detection algorithm dilates, erodes and restores, Fourier transforms, bandpass filters, thresholds, skeletonizes, line traverses and interpolates the data for each of the two images. Then, the resulting information is normalized to eliminate the effects of the patient's ocular optics on the captured images. A topographic line map is then constructed using the information from each of the two images and the map is divided into sections for analysis. The computer then registers the map with topographic maps constructed from images acquired on previous patient visits using selected landmarks. Volumetric changes in the topography of the retina as compared to prior topographies for the patient are calculated, and, with other quantities of interest, are displayed in an easily-interpreted report. The apparatus may also be used for color fundus photography, fluorescein angiography, or indo-cyanine green angiography.

DETAILED DESCRIPTION OF THE PREFERRED EMBODIMENTS

The present invention is a system and method for topographical analysis of the retina, and particularly the optic nerve head.

Figure 1:
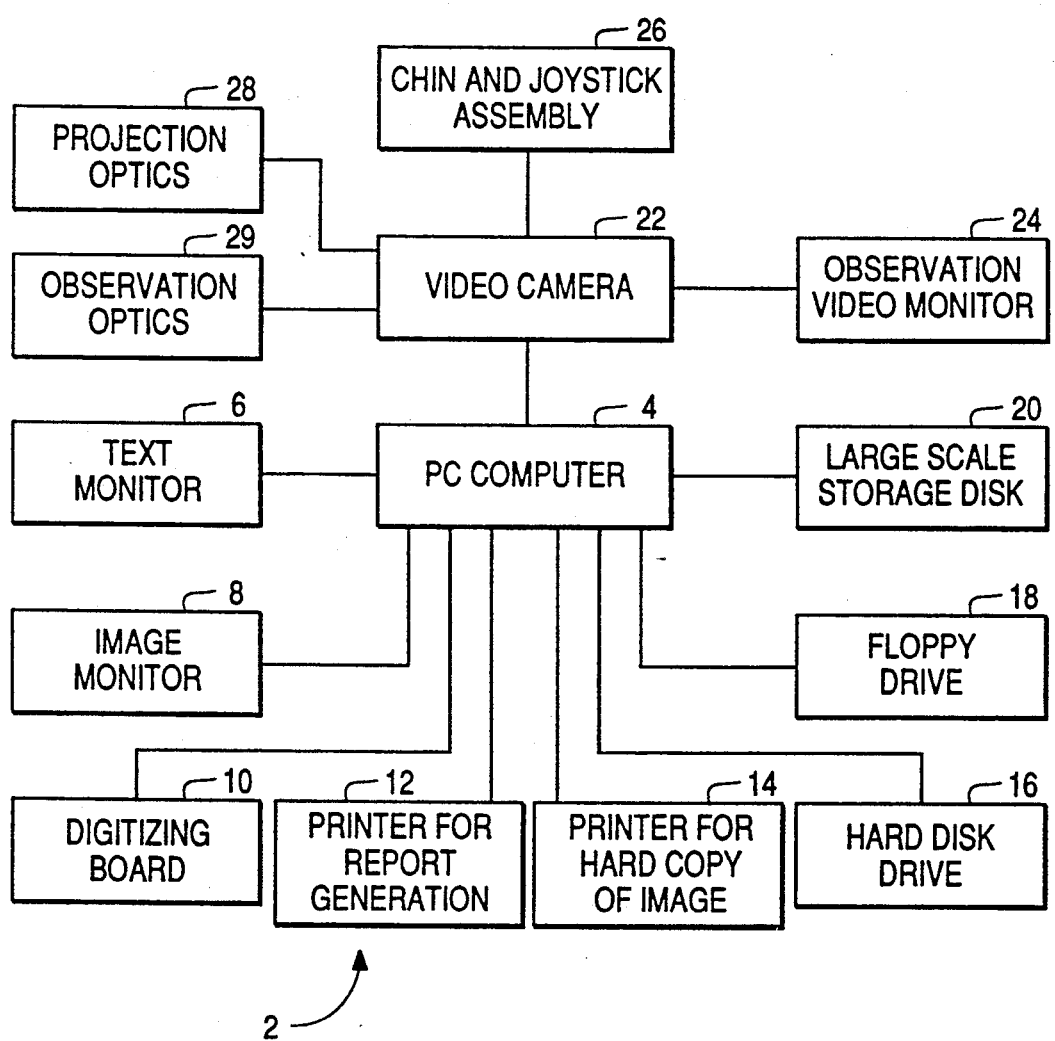
FIG. 1 is a block diagram of the apparatus of the present invention.

Referring now to FIG. 1, the topographical analysis apparatus of the present invention is shown generally at 2. A personal computer 4 forms the center of the system, processing data and controlling the operation of other components of the system. Connected to the personal computer 4 are a text monitor 6, an image monitor 8, a digitizing board 10, report printer 12, image printer 14, hard disk 16, floppy disk 18, large-scale storage disk 20, and video camera 22. The components connected to personal computer 4 may be located either inside or outside a case holding personal computer 4. An observation video monitor 24, a chin and joystick assembly 26, projection optics 28, and observation optics 29 are associated with the video camera 22.

The personal computer 4 is preferably a compact computer of relatively high processing power using a standardized operating system and having standardized card slots for interfacing peripheral equipment such as digitizing board 10, printers 12 and 14, hard disk 16, floppy disk 18, large-scale storage disk 20, and monitors 6 and 8. For example, the personal computer may incorporate an Intel 80386-SX processor operating at a clock speed of at least 16 Mhz, and be software-compatible with personal computers manufactured by IBM Corporation. Of course, other computers and processors of similar or greater power could also be used, such as micro-computers, mini-computers, and workstations manufactured by Apple Computer, Sun Microcomputer, Digital Equipment Corporation, and others. The personal computer 4 will run customized retinal analysis software as will be described in detail later. Preferably the personal computer 4 will be equipped with a pointing device such as a mouse for making menu selections to control operation of the retinal analysis software. The personal computer 4 may also be equipped with an auxiliary array processing board, a numerical coprocessor, and/or a digital signal processing board to increase numerical processing speed. The selection of these auxiliary processing units will depend on the processing capacity of the personal computer 4 that is selected and the speed of analysis that is desired for the system.

Text monitor 6 is a conventional computer monitor which has at least textual display capability, and will be used, as explained in detail later, primarily for displaying menus and other status and control information regarding the topographical analysis apparatus 2. The image monitor 8 will preferably be a very-high-resolution color graphics monitor appropriate for displaying images under analysis. A monochrome monitor could also be used to further reduce the cost of the system.

The digitizing board 10 accepts a standard video input from video camera 22 and functions as a "frame grabber." That is, when activated by a signal from the personal computer 4, the digitizing board will collect analog video signal data from video camera 22 at that instant and render the analog video signal into digital data. The digital data produced by digitizing board 10 in response to the actuating signal from personal computer 4 is stored in a memory and made available to personal computer 4 for analysis. Digitizing board 10 may be a conventional device, such as for example a model number PIP-10240B board manufactured by Matrox Co.

Report printer 12 and image printer 14 are preferably relatively high-speed printers capable of high resolution graphics output, such as laser printers. If desired, report printer 12 and image printer 14 could be implemented using a single printer capable of performing both functions.

The large-scale storage disk 20 is preferably a laser read/write disk drive or an optical WORM drive capable of storing large amounts of data, such as on the order of 800 megabytes of data. Although a large-processing scale storage disk 20 that operates optically is preferred, large-scale storage devices operating on other principles could also be used. The important characteristics which should be examined in selecting the large scale storage disk 20 are capacity and access speed. As will become apparent when the operation of the system is described in detail, the capacity of the large scale storage disk 20 should be large in the present application, so that data describing several previous measurements of the patient's retinal contours can be accessed, and so that a large number of patients can be served by the system. The access speed of large scale storage disk 20 should be high so that waiting time for obtaining prior patient data is minimized. As will be seen when the operation of the retinal analysis software is described, it is desirable that prior data be obtained for comparison and a report generated immediately upon completion of the topographical scan performed by the topographical analysis apparatus 2.

Figure 2:
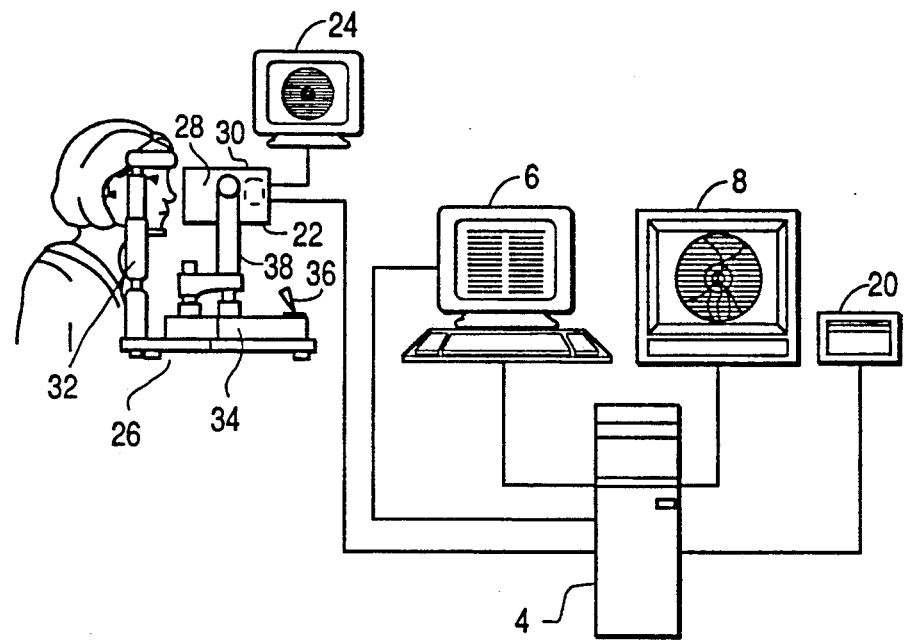
FIG. 2 is a diagram showing the apparatus of the present invention.

FIG. 2 shows the major parts of the topographical analysis apparatus 2 as they appear in use. The personal computer 4 is shown in a tower-type case which incorporates interfaces for text monitor 6, image monitor 8, large scale storage disk 20, and the printers 12 and 14 (not shown in FIG. 2). In addition, personal computer 4 has in internal slots the digitizing board 10, the hard disk 16, and the floppy drive 18. The video camera 22 is connected to the digitizing board 10 and to the observation video monitor 24. The video camera 22, the projection optics 28, and the observation optics 29 form an optical subsystem of the apparatus 2 and are located in a common housing 30 which is mounted on chin and joystick assembly 26.

Chin and joystick assembly 26 is a device for interfacing the video camera 22, projection optics 28, and observation optics 29 to the patient's eye. Chin and joystick assembly 26 comprises head support 32, movable base 34, joystick 36, and housing support 38. The head support 32 holds the patient's chin and forehead in a known, fixed position. The head support 32 is provided with elevation adjustments to provide a comfortable resting place for the patient's head. The position of housing 30 relative to the head support 32 can be adjusted in both gross and fine increments using the joystick 36. A suitable chin and joystick assembly 26 is the one used for the Kowa Handheld Fundus Camera, available from Kowa Optimed of Japan.

Figure 3:
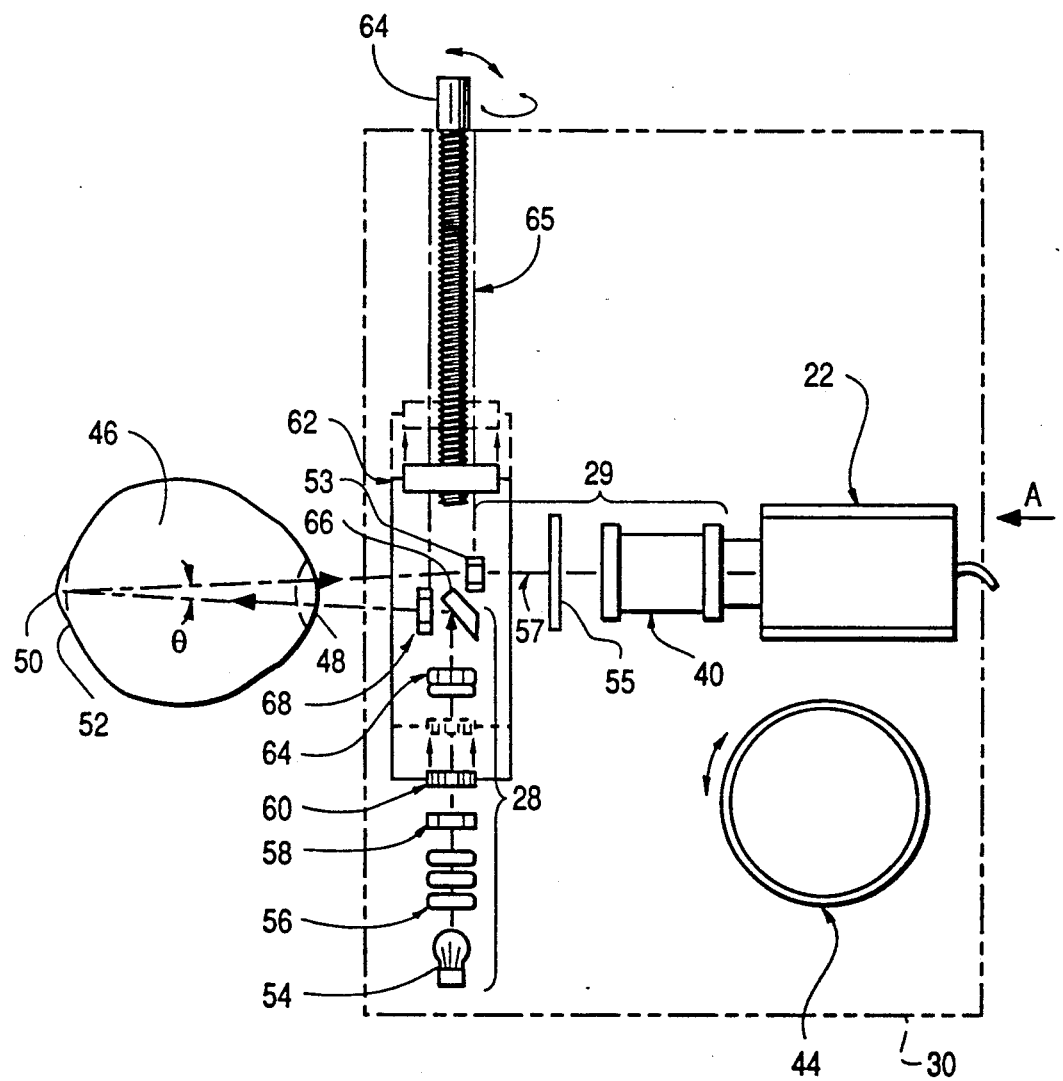
FIG. 3 is a side view assembly diagram of the optical unit of the chin and joystick assembly of the present invention.

Referring now to FIG. 3, the housing 30 containing the video camera 22, the projection optics 28, and the observation optics 29 is shown in side sectional view, proximate to a sectioned eyeball 46 having a cornea 48 and a retina 52, with the retina 52 including optic nerve head 50. Housing 30 may be cylindrical or of another appropriate shape.

As will be seen, the structure of the housing 30, which has no forward protruding parts, prevents accidental direct contact of any part of the apparatus with the patient's cornea during movement of the housing 30 relative to the patient's eyes. This feature of the present invention is particularly advantageous in that a number of prior art methods of acquiring optic data require that optics approach the cornea closely to accomplish the tasks of examination and image capture. The external housing 30 and the optics therein, by contrast, has been designed to maintain some distance to the cornea, increasing patient comfort while the test is being performed. If desired, a flexible interface such as a rubber cup could be provided at the interface between the housing 30 and the patient's face.

The inclusion of projection optics 28, observation optics 29 and video camera 22 in a single compact housing provides a high degree of repeatability, overcoming a significant weakness of prior art devices designed for attachment to a fundus camera. By placing all elements of the system in one housing, error that could be induced by variations in projection angles are eliminated. Additionally, the miniaturization of design compared to that of a fundus camera for observation and image capture provides for a shorter and more light efficient optical pathway. The compact design and simplicity of optics reduces production costs and permits greater ease of use by the operator.

Video camera 22 is preferably compact and incorporates a black-and-white charge-coupled device type image sensor. A suitable camera is a Cohu model 6400. The video camera 22 has a lens 40 which is a 25 mm F1.7 lens. An image focus knob 44 accessable from the outside of housing 30 is connected to the lens 40 associated with video camera 22 by conventional optical gearing mechanisms to allow focusing of the lens 40 on the optic nerve head 50. The focusing of lens 40 by means of image focus knob 44 will compensate for the optics of eyeball 46 as well as compensating for variations in the distance from lens 40 to the optic nerve head 50. Lens 40 may be focused manually by observing the image displayed on observation video monitor 24 while adjusting image focus knob 44 until a clear, focused image is obtained on observation video monitor 24. Alternatively, an electronic autofocusing control system could be provided for automatically adjusting the focus of lens 40.

The video camera 22 could also be a color video camera if desired. Providing a color video camera 22 would permit the apparatus 2 to be used for color fundus photography in addition to the other functions disclosed herein. Thus, with a color video camera 22, the multifunctional nature of the apparatus 2 is further enhanced.

The observation optics 29 associated with the video camera 22 include the aforementioned lens 40, an observation aperture 53, and a filter 55. The observation aperture 53 and the filter 55 transmit light reflecting from the retina 52 to the lens 40 and hence to video camera 22. The filter 55 is a custom infrared blocking filter which improves the contrast of the image seen by the video camera 22. The infrared blocking filter 55 preferably has transmission of greater than or equal to 75% AVG at 400-600 Nm and transmission of less than or equal to 2% AVG in the range from 675-2000 Nm.

If it is desired to use the apparatus 2 for indo-cyanine green angiography, color fundus photography, or fluorescein angiography, in addition to glaucoma diagnosis as will be described herein, additional filters may be provided as appropriate for these functions. These filters will be mounted so as to be selectively rotatable in and out of the view axis of the video camera 22 according to the function being performed. The rotation may be accomplished manually or under computer servo control.

The projection optics 28 of the present invention projects a series of parallel lines onto the retina 52, off axis at an angle Theta from the line between the center of optic nerve head 50 and the central axis 57 of lens 40 of video camera 22. The image of the projection of these parallel lines then passes back through observation optics 29 to the video camera 22 and is then analyzed by the personal computer 4 attached to the video camera 22 in a manner that will be explained in detail later.

The projection optics 28 comprise a lamp 54, lamp lens group 56, grid aperture 58, grid 60, grid carrier 62, grid knob 64, optics 64, mirror 66, and projection aperture 68. A control (not shown) is provided to adjust the intensity of the lamp 54, either manually or under the control of personal computer 4.

Parallel lines are projected by projection optics 28 in the following manner. Light from lamp 54 passes through the series of lamp lens group 56, consisting of three lenses. The lenses of lamp lens group 56 concentrate the light output of lamp 54. Lamp lens group 56 may preferably consist of three achromatic lenses of 8 mm, 12 mm, and 12 mm focal length located sequentially with the 8 mm lens closest to the lamp 54. Next, the light passes through grid aperture 58 which concentrates the light and then through the grid 60. The grid 60 is a rhonchi ruling with a 3:1 dark to light ratio. The clear areas (lines) are preferably 1/200 of an inch wide, and the opaque areas (space between projected lines) are preferably 3/200 of an inch wide. The grid 60 provides a parallel line light output. From grid 60, the parallel line light passes to optics 64 which consists of a lens and an aperture that work together to focus the projected grid on the retina 52. The lens of optics 64 is preferably an acromatic lens of 20 mm focal length.

The light is then deflected by mirror 66 which is placed at a critical pitch angle relative to the video camera 22 and the projection optics 28 so as to project the parallel lines produced by projection optics 28 at the angle Theta relative to the line between the center of retina 52 and the central axis 57 of lens 40. The angle of separation Theta of the mirror and the pitch of the mirror are critical to the proper functioning of the instrument of the present invention. Preferably, the angle Theta may be approximately 8 degrees. A larger angle Theta might also be used, but an angle Theta of 8 degrees works well in the prototypes that have been constructed.

The light passes from the mirror 66 through projection aperture 68 which concentrates the light. The light then passes through the cornea 48 and is projected onto retina 52 and in particular the optic nerve head 50 of retina 52.

All the apertures used, such as apertures 58, 64, and 68, and the aperture of optics 64, may be 3 mm apertures. Although the lamp 54 has been described as a generalized lamp, it should be noted that the lamp 54 might be any source of radiant energy. In one preferred embodiment, the lamp 54 is an infrared illumination source, and the specifications of filter 55 are adjusted accordingly to pass the wavelength of the lamp 54. Infrared illumination may be particularly desirable for acquiring images without the problems generated by lack of pupil dilation. The image can be captured in a relatively dark room using infrared illumination, so that the eye being imaged is naturally dilated. In another preferred embodiment which addresses the problems caused by lack of pupil dilation during imaging, the lamp 54 may be strobed during image acquisition rather than being kept on constantly, thereby preventing the energy of lamp 54 from narrowing the pupil prior to image capture. It should also be noted that, regardless of whether these methods are employed, the system of the present invention is superior to prior art systems. Because of the unique design of the projection optics 28 and the capabilities of the image analysis software employed, useful image data can be collected with minimum pupil dilation. Specifically, the pupils of the eye being imaged may have a diameter of as little as 3.5 mm.

The grid 60 is carried in the adjustable grid carrier 62 riding in an adjustment track. The position of grid carrier 62, and thus grid 60, can be adjusted relative to the other components of projection optics 28 by turning grid knob 64. The movement of grid 60 relative to the other components of projection optics 28 is used by the operator to compensate for variations in distance between the projection optics 28 and an individual retina, as well as compensating for the optic properties of the cornea 48, thereby focusing the projected parallel lines on the retina. The grid adjustment system disclosed herein, including grid knob 64 and grid carrier 62, is the most economical means of adjusting the position of the grid 60 and is therefore the preferred embodiment. However, those skilled in the art will recognize that it is also possible to provide an autofocus system for focusing the parallel lines that are projected on the retina 52 by projection optics 28.

To obtain a plurality of images of the optic nerve head 50 with the lines projected through grid 60 at different orientations, the projection optics 28 may be rotatable about the central axis 57 of video camera lens 40. The rotation of the projection optics 28 about axis 57 may be accomplished by mounting the components of projection optics 28, including lamp 54, lamp lens group 56, grid aperture 58, grid 60, grid carrier 62, grid knob 64, optics 64, mirror 66, and projection aperture 68, to a carrier which is mounted in the housing 30 to pivot about axis 57. Grid knob 64 may be mounted so as to protrude from a slot 65 about the circumference of housing 30, the plane containing the slot 65 being perpendicular to the axis 57. By moving the grid knob 64 about the circumference of housing 30 within the slot 65, the operator can rotate the projection optics 28 so that the orientation of the lines projected by projection optics 28 and their direction of projection relative to the axis 57 are varied. In the position shown in FIG. 3, the lines are projected from below the axis 57, appearing horizontally on the retina 52. If the grid knob 64 is rotated 90 degrees clockwise in the slot 65, as seen from an observation point A along the axis 57 and facing the eye 46, so that the grid knob 64 is horizontal and to the left as seen from point A and the lamp 54 is rotated out from the surface of FIG. 3 and is thus horizontally to the right of point A, the lines projected by the projection optics 28 would be projected from the left of the axis 57 and the lines would appear vertically on the retina 52. Thus, grid knob 64 serves two functions in that it may be moved clockwise or counterclockwise in the slot 65 as seen from point A to rotate the projection optics 28 about axis 57, or grid knob 64 may also be rotated about its own central axis to move grid carrier 62 relative to the other components of projection optics 28 and thus focus the lines projected by projection optics 28 on the retina 52.

The slot 65 may be provided with any number of stops or detents as desired, preferably at the points just described where the grid lines are projected horizontally and vertically on the retina 52. In this embodiment the slot 65 need only span an arc of 90 degrees; however, the slot 65 could also permit any other rotation of the projection optics 28, including a complete 360 degree rotation about the axis 57 if desired. The manual rotation of the projection optics 29 as described using grid knob 64 is preferred to minimize construction costs of the system so that the system can be economically available in each optometrist's or opthalmologist's office. However, the rotational function of grid knob 64 could also be automated, using a solenoid or a stepper motor, and an electrical control on the outside of housing 30 could be provided for controlling the rotation of the grid. Such an automated system could rotate the projection optics 28 selectively to predetermined positions, such as for projecting horizontal and then vertical parallel lines on the retina 52. An automated rotation device of this type could also be controlled by the software of personal computer 4.

Finally, to facilitate multifunctional use of the apparatus 2, such as for color fundus photography, fluorescein angiography and indo-cyanine green angiography, the grid 60 may be mounted so that it can be rotated out of the path of projection optics 28 so that radiant energy is projected on the eye directly and not in a grid pattern. In addition, multiple lamps 54 or filters for varying the characteristics of the energy transmitted through projection optics 28 may be provided where necessary or desired to facilitate multifunctional use of apparatus 2.

Figure 4:
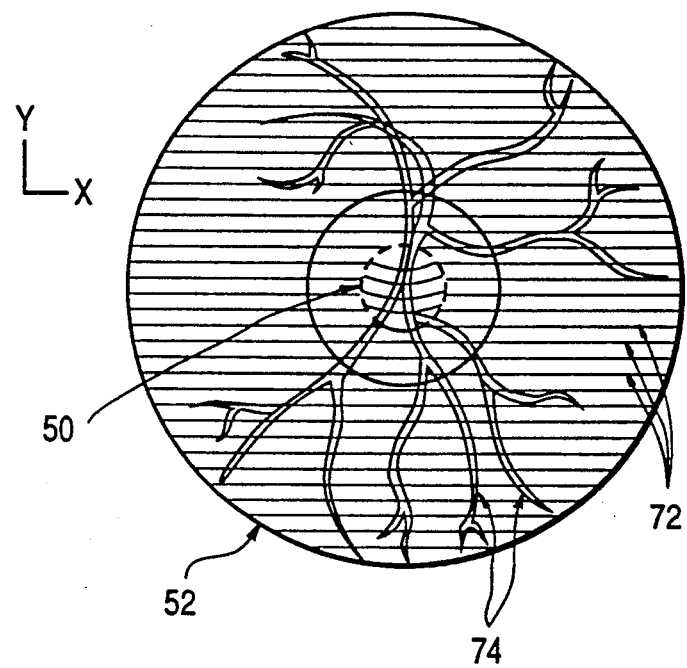
FIG. 4 is a drawing of a retina with horizontal parallel lines projected by the apparatus of the present invention.

As just described, the projection optics 28 of topographic analysis apparatus 2 project a series of parallel lines onto the retina 52 off axis from the observation path of video camera 22. FIG. 4 shows the retina 52 as seen by video camera 22 with horizontal parallel lines 72 projected on retina 52 by the projection optics 28. The video camera 22 also sees blood vessels 74 of the retina 52. Because the parallel lines 72 are being projected onto the retina 52 off axis relative to the view of video camera 22, the lines distort as they pass over the topography of the optic nerve head 50 and the projected lines are then captured by video camera 22 and the image is digitized by a digitizing board 10 in the personal computer 4.

Figure 5:
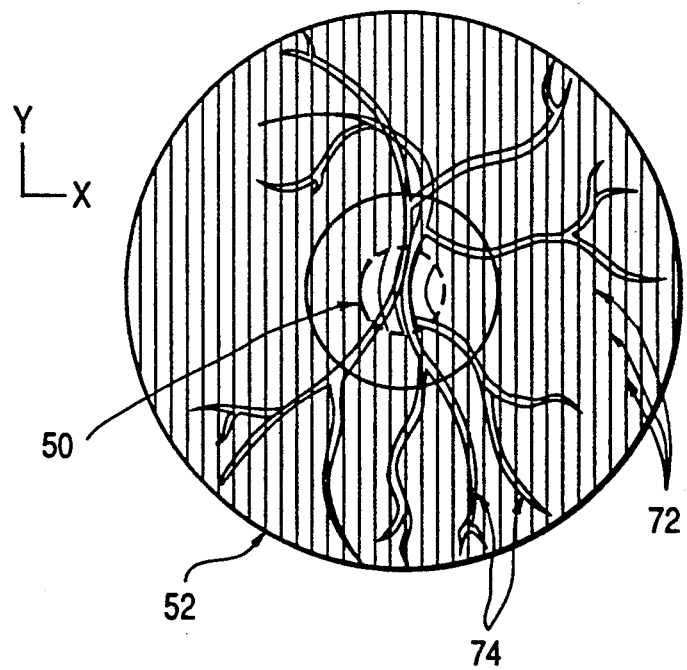
FIG. 5 is a drawing showing the retina of FIG. 4 with the line projection rotated 90 degrees so that vertical parallel lines are projected.

FIG. 5 shows the same retina seen in FIG. 4. The projection optics 28 have been rotated 90 degrees so that the parallel lines 72 are projected vertically on the retina 52 from a different direction. In general, two images as shown in FIGS. 4 and 5 may be captured and digitized by the apparatus, with the parallel lines 72 rotated 90 degrees between image captures as shown in FIGS. 4 and 5. The process may preferably be repeated for each of the patient's eyes, so that a total of four images are captured in an office visit. Of course, any larger or smaller number of images could also be taken as desired, with a corresponding increase or decrease in the absolute accuracy of topographical maps produced from the data collected.

The operation of the software running on personal computer 4 will now be described in detail. The software captures images, analyzes the images in comparison with images collected and stored on previous visits by the same patient to determine whether changes have occurred in the volume of the optic nerve head. The software package running on the personal computer 4 allows easy databasing and archiving of patient data and storage of data on either floppy drive 18 or large scale storage disk 20. Generally, data for all patients visiting a single office would be stored on the large scale storage disk 20 so that it is not necessary to catalog and store a large number of floppy disks. However, patient data may also be stored on floppy drive 18. Floppy disk data storage may be desirably if the patient is to be seen by a doctor at a different location. Of course, the personal computer 4 could also be provided with a modem and the software could be provided with a menu selection to transmit patient data to another office having equipment compatible with topographical analysis apparatus 2.

Figure 6:
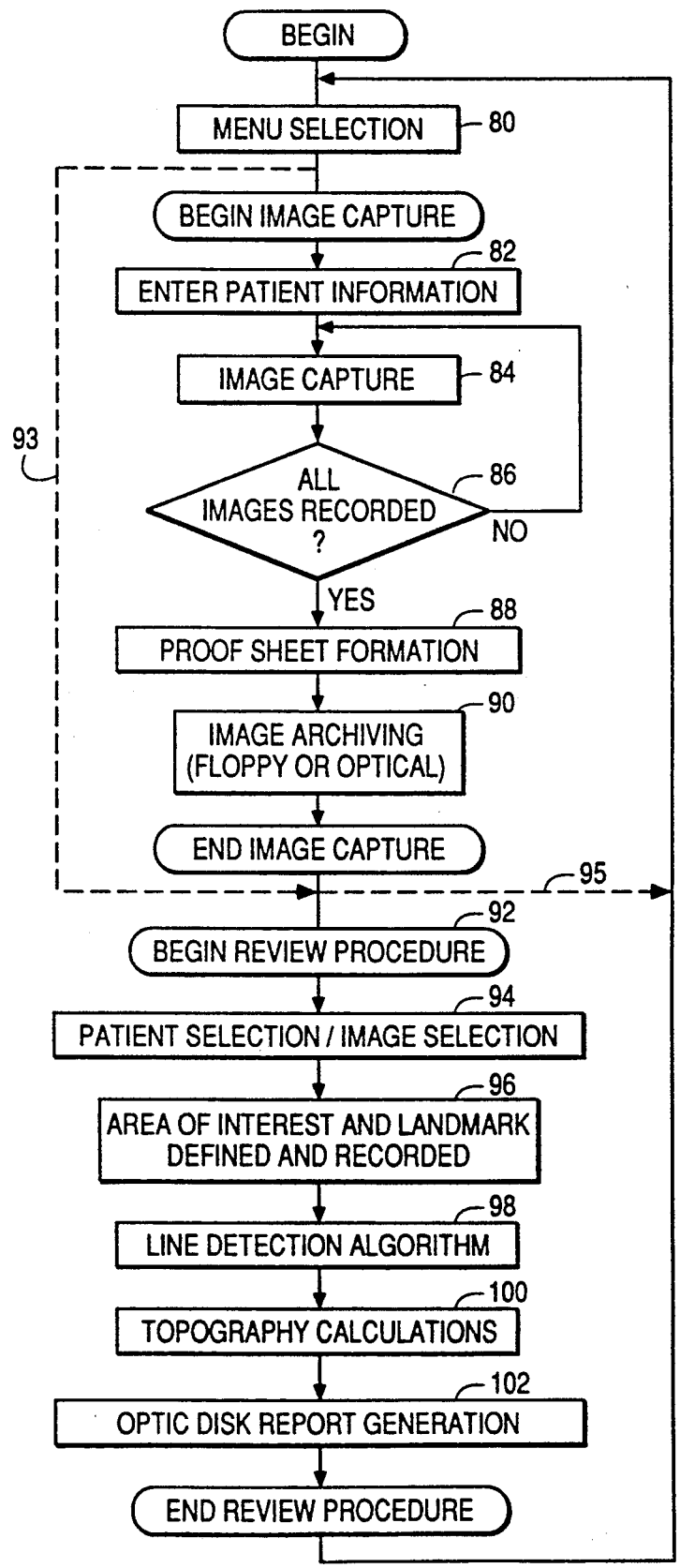
FIG. 6 is a flowchart showing the steps of the screening operation performed by the apparatus.

FIG. 6 is a flowchart showing the steps in the operation of the software. In the first step, menu selection step 80, the software displays a menu on text monitor 6 and accepts operator input to select a function. The software is preferably entirely menu-driven to promote ease and speed of operation. To perform a procedure an operator simply makes a menu selection to select the desired procedure in step 80. While the software and operation of the system will be described herein in terms of cataloging images and performing glaucoma diagnosis using the image data, it will be understood that other diagnostic and evaluation functions can be performed using the same apparatus and using portions of the same software. These other diagnostic and evaluation functions may also be provided as menu choices. In addition, further menu choices may be provided for file maintenance, including transferring and receiving patient data between offices, deleting patient files, editing patient data, and transferring patient files between hard disk 16, floppy drive 18, and large scale storage disk 20. Other necessary and desirable functions can also be provided as menu choices. For example, the software may also be designed to perform color fundus photography, fluorescein angiography, and indo-cyanine green angiography in conjunction with the apparatus 2.

The software next prompts for patient information, such as name, identification number, name of the patient's physician, age, etc. as shown in block 82, "enter patient information." If the patient has been evaluated by the present apparatus before, so that this information is already present in large scale storage disk 20, a search may be conducted of the database in large scale storage disk 20, for example by patient name or by i.d. number, to obtain the remaining patient information and to identify the previous records of the patient existing in the system. This method of obtaining patient information by searching the database ensures that the images taken during this visit are correlated with the previous images associated with the same patient.

The software then awaits an indication that the patient is prepared and the optics are focused. The patient places his or her head in the chin and joystick assembly 26 so that the patient's head is held substantially immobile. The operator adjusts the position of housing 30 using adjustments on the chin and joystick assembly 26 and particularly using the joystick 36 until the projection optics 28 and the video camera 22 are aimed through one or the other of the patient's corneas 48 to the retina 52 of the eye 46. While referring to the observation video monitor 24, the operator then adjusts image focus knob 44 and grid knob 64 until the observation video monitor 24 shows a reasonably clear image of the parallel lines 72 projected on the retina 52. If an autofocus system has been provided, the operator would indicate, such as by pressing a function key on personal computer 4 or a button near housing 30, that the housing 30 is in position. In response to this indication, the autofocus system would then focus the grid and the image to provide a clear image to video camera 22 of the parallel lines 72 projected on the retina 52.

Image capture is triggered by the operator as shown in block 84 by the operator pressing a button on the joystick or triggering a foot pedal to signal the personal computer 4 that the image of video camera 22 should be recorded. In response to the indication of the operator that the image should be recorded, the personal computer 4 will cause the image of video camera 22 to be digitized by digitizing board 10 and will then store digital data representing the captured image temporarily on hard disk 16.

Preferably, two images of the same retina 52 will be captured, with the grid 60 being rotated 90 degrees between images so that the parallel lines 72 are oriented in the second image perpendicularly to their orientation in the first image. The parallel lines 72 in the two images will be rotated 90 degrees between images as illustrated in FIGS. 4 and 5. Obtaining a plurality of images with the parallel lines 72 oriented differently compensates for the tendency of irregularities in the topography of the optic nerve head 50 to shade adjacent portions of the optic nerve head, thus preventing formation of a complete topographical map of the optic nerve head 50 based on a single image. As will be seen, the method of analysis of the image data is substantially linear. Thus, the information provided by two images having parallel lines 72 at different orientations is maximized when the parallel lines 72 are oriented along the X-axis of the plane of optic nerve head 50 in one image and along the Y-axis of the plane in the other image. The multiple image data will be correlated by the personal computer 4 and the total information provided by all the images taken at one time will be used to define a single topographical map of the optic nerve head 50. Of course, more than two images at different angles could be taken if desired, but two images are sufficient to provide the necessary information to define an accurate topographical map of the optic nerve head 50.

The operator can rotate the projection optics 28 using grid knob 64, and can then cause the newly prepared image to be captured by again pressing a button or foot pedal. This process continues according to the alternate path provided by block 86 of FIG. 6 until the last desired image has been captured. Alternatively, this process could be automated if the grid 60 could be rotated mechanically under the control of personal computer 4 as described previously. Upon the operator's pressing the indicator button or foot pedal for the first time, the software of personal computer 4 could capture a first image, rotate projection optics 28, and capture a second image, and might repeat this process further if desired. An automated method would be advantageous in that the entire process of image capture would occur in a fraction of a second, so that little movement of the eye 48 would occur between subsequent images. Thus, correlation of sequential images to form a single topographic map would be simplified.

The images captured are then displayed in proof sheet format for easy selection and review, as shown in block 88, "proof sheet formation." In the proof sheet format, a plurality of the images captured, preferably up to 16 images can be presented at the same time in windows on image monitor 8. The proof sheet format display allows review of the images to ensure that they are acceptable. For example, if the patient blinked or moved during the capture of an image, or if focusing controls were not adjusted properly, a captured image might be unacceptable for analysis purposes. On viewing the proof sheet format display, the operator would note the problem with the image. Although not shown in the flowchart for clarity, the software of personal computer 4 will permit a return to the image capture block 84 and thereby allow replacement of certain captured images if the operator indicates that some of the captured images are unacceptable.

Permanent storage of the images will be either on floppy drive 18 or in most cases on large scale storage disk 20, as shown in block 90, "image archiving." The images will be stored in records including header information, such as the patient identifying data described previously, and further including date and time stamps. The image records will also include the image data, which may be stored in the format produced by the digitizing board 10. Alternatively, the image data might be stored in any of a number of standard image data formats used by commercially available software. Storage in one of these formats would enable use of this other software to manipulate the images.

The permanent image storage preferably includes both the complete image data and the topographical map data for the image, which is calculated as will be explained in detail later. The storage of both the complete image and the topographical map data permits faster analysis since for comparison to the present state of the retina 52 it may only be necessary to access the topographical map data, which is less voluminous than the complete image data. Of course, if permanent image storage space is limited, the topographical map data alone might be stored, with the total image data being discarded. But if space is available, it is preferred to store both types of data for each image record since it is desirable to be able to display an image of the retina 52 as it appeared at prior visits, and since it is also desirable to avoid the necessity of reprocessing each of many stored images for a patient to create a topographical map thereof at each office visit so that the topographical maps can be compared as will be explained below.

Once the images have been stored in the personal computer 4, the software of personal computer 4 can perform a review procedure or analysis beginning with block 92 of the flowchart, or alternatively control can be returned to the menu selection block 80 by path 95. If the review procedure beginning with block 92 is to be performed, the first step in this review procedure is selection of the patient and the images to be used in the analysis (Block 94). In most cases, the analysis will be performed immediately following the image collection, and the images used will be the images just captured and any prior images stored on the system during the patient's previous visits. In this default case, the keystrokes required to continue and perform the analysis will be minimal. For example, a function key could be pressed or the mouse could be clicked on a menu item to perform analysis for the patient just imaged. However, the software will allow analysis of a patient's data independent of the image capture process. Thus, the review procedure beginning in block 92 can be accessed through the software menus via path 93 and may thus be performed at any time for any patient. If a default patient and data are not present on the system by reason of images having just been captured for a patient by execution of blocks 82 through 90, the patient and the images relating to that patient that are to be used must be selected manually or by searching the database by the operator in block 94.

Next, as shown in block 96, the area of interest must be defined. The operation of the system herein has been described in terms of analysis of the optic nerve head 50, which will be the area of interest in this case. However, those skilled in the art will recognize that the apparatus and computer techniques disclosed can be readily applied to topographical or volumetric analysis of other ocular regions. Therefore, the software may preferably permit options other than analysis of the optic nerve head 50 and glaucoma diagnosis thereby. The software will preferably display images on the image monitor 8 and allow the operator to place a box around an area to define the area of interest. As part of this step, the operator will also identify and mark one or more particular landmarks, such as distinctive topographic features in optic nerve head 50, blood vessels, etc. The same landmarks should be used in analyzing all images associated with a particular eye so that the various sets of image data can be registered or correlated with respect to the landmark or landmarks selected. Thus, the area of interest is selected and particular landmarks in the area are identified for use in data matching between images. In the landmark selection step, the operator may call up previously collected images of the same eye for display on the image monitor 8, either singly or in proof sheet format, to determine which landmarks were used in prior analysis. Of course, landmark identification could also be carried out automatically by the software, or the software could "suggest" landmarks that appear appropriate for use in registering the various images with respect to each other.

The next step (Block 98) is analysis of the images using novel and unique line detection algorithms to determine the perturbations of the parallel lines 72 as they are projected onto the area of interest, and thus map the topography of, for example, the optic nerve head 50. It is a particular advantage of the present invention that the algorithms used for line detection permit the line detection and analysis to proceed almost independently of the image quality or sharpness of the line. In general, one-dimensional image processing will be used, in which the pixels of the images are analyzed in a linear fashion by the row or column. These linear, one-dimensional processes are performed for each row or column of the image, as applicable. Each of the one-dimensional processes are preferably performed either in the same direction as the parallel lines 72 appearing in the image, or perpendicular to the parallel lines 72 appearing in the image, as appropriate. Because the interline spacing of the parallel lines 72 is known, the approximate location where a bright spot or line should appear is known as each of the one-dimensional processes are performed, scanning either across or along with the parallel lines 72. This "expectation information" about where lines should appear can be used profitably in conjunction with the information contained in the image data. Even if the images are relatively less clear than that obtained by more sophisticated and expensive optical apparatus, it is possible with the present apparatus and software to obtain line identification and analysis of the same or better quality as that produced by prior art instruments. By combining the information available on line spacing with the information provided by a first image with horizontal parallel lines 72 (FIG. 4) and a second image with vertical parallel lines 72 (FIG. 5), it is possible to create an accurate topographical map of the optic nerve head 50 without the need for sophisticated optical projection systems for projecting parallel lines 72 in perfect focus on the retina 52 over a relatively wide depth of field. The apparatus of the housing 30 would not provide an input of quality acceptable for use with prior art analysis systems, but the present apparatus, when used to collect two or more images with differing parallel line orientations and when used with the algorithms disclosed herein, provides a superior result at less expense.

One-dimensional image processing also requires less calculation than two- or three-dimensional image processing. The reduced processing time required by these algorithms is another particular advantage of the present invention since it is an object of the invention to provide a relatively inexpensive yet accurate analysis system which can be made widely available in opthalmic offices. Since fewer calculations are required in the method of the present invention as compared to prior art methods, a readily available and relatively inexpensive personal computer 4 can be used in the system.

The line detection algorithms of the present invention will be performed for each image that is to be included in the analysis. For the sets of two images taken in the same sitting with different orientations of parallel lines 72 as described previously, the algorithms will be used to process each of the two images independently. Later, when a single topographical map of the optic nerve head 50 is to be formed using the line information obtained from the two images, the information will be combined.

The algorithms operate on the principle that, since parallel alternating dark and bright stripes are being projected onto the optic nerve head from one angle and being viewed/imaged from a different angle, the deviation of these lines from straightness are related to the topography of the optic nerve head at the point of deviation. As noted previously, an image is acquired with parallel lines 72 oriented horizontally followed by a second image with parallel lines 72 oriented vertically. These images are analyzed for the purpose of generating a function which relates the line shift in pixels to various points on the nerve head. The line detection algorithm 98 digitally identifies the locations of the projected lines and is the first step in this analytical process.

The parallel lines 72 are roughly parallel on the image in the horizontal and vertical directions in each image. This orientation is advantageous in that a 1-dimensional enhancement and analysis of the columns and rows of image data in respective images can be performed.

Figure 7:
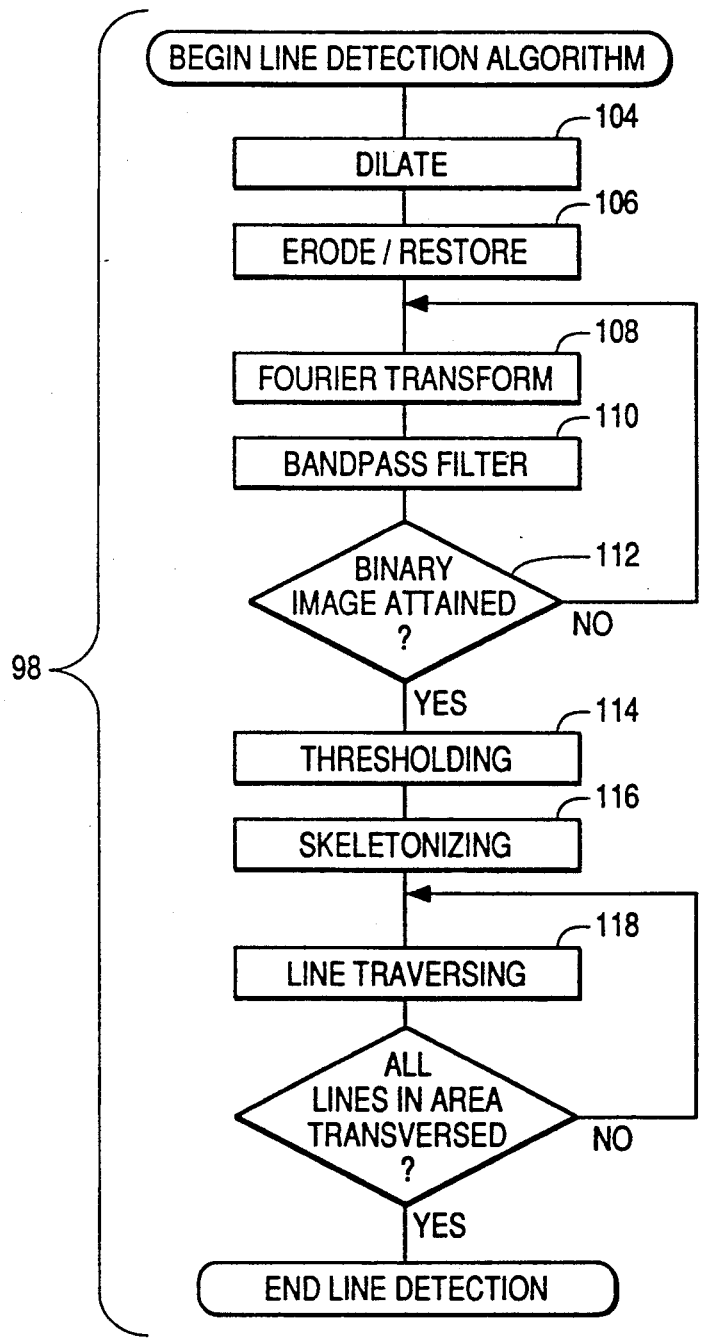
FIG. 7 is a flowchart showing the line detection algorithms of the present invention.

Referring now to FIG. 7, a flowchart of the line detection algorithms of block 98 in FIG. 6 is shown. The line detection algorithms begin at block 104 by performing a one-dimensional dilation on the data to eliminate any blood vessels 74 from the image. Eliminating the blood vessels from the images is desirable prior to further line detection analysis since the outlines of blood vessels 74 may be confused with the lines which are to be detected, leading to erroneous line location and finally producing an inaccurate topographical map. Dilation in this case is a process which reduces the size of black areas of the image and correspondingly increasing the size of white areas of the image. Because blood vessels in the eye 46 tend to appear as black spots in the image, the dilation process tends to reduce the prominence of blood vessels in the image. Since the direction of the parallel lines 72 for the image is known, the dilation will be performed only for black areas running in a direction other than the direction of parallel lines 72 so that parallel lines 72 are not widened so as to eliminate the dark areas between parallel lines 72. For blood vessels running parallel to the parallel lines 72, the software may evaluate the digitized light levels registered in the pixels of these areas. Blood vessels will appear as an even darker shade than the dark areas between parallel lines 72. This contrast, although less than the contrast between (1) the parallel lines 72 and (2) the dark areas between the parallel lines 72, could be used in a second dilation process which would operate to eliminate these darker blood vessel areas from the dark areas between parallel lines 72, leaving dark areas of a single level of darkness between the parallel lines 72.

A one-dimensional erode function which restores the image structures to their original geometry (block 106) is then performed as part of the process of eliminating blood vessels 74 from the images. As described previously, the dilation process of block 104 tends to enlarge the white areas of the image. The erode process is generally the inverse of the dilation process in that the erode process reduces the size of white areas and enlarges the size of black areas in the image. The one-dimensional erode and restore process thus restores the correct geometric shapes of the image, following the dilation performed in block 104.

The one-dimensional dilation of block 104 and the erode and restore of block 106 are preferably performed transverse to the orientation of the parallel lines 72 in the image being processed. That is, if the parallel lines 72 are vertical, the one-dimensional processing of blocks 104 and 106 will be performed horizontally, and if the parallel lines 72 are horizontal, the one dimensional processing will be performed vertically.

Next, as shown in blocks 108 and 110, one-dimensional fast Fourier transforms and band pass filtering are iteratively performed on each column or row of image pixel values, eliminating excess information in the image so that only the line spacing frequency neighborhood is retained. This step is performed in multiple passes until a substantially binary image is obtained according to block 112. On attainment of the binary image according to block 112, remnant lines in the image for which lines are being detected approach a binary image (black and white). The Fourier transforms and bandpass filtering to be used are chosen relative to and depending on the separation of the lines in grid 60. Specifically, the processes of blocks 108 and 110 are designed to select information appearing at the frequency of the line spacing of parallel lines 72, which appear as spaced bright spots along the one-dimensional line of analysis, and to deemphasize and eventually eliminate information appearing at other frequencies. For example, with a 512×512 pixel display, approximately 20 parallel lines may be projected across the image captured. Thus, it is desired to enhance image data which occurs at about a frequency of 20 Hz across the width of the image and to deemphasize image data occurring at frequencies substantially different from 20 Hz. The wavelength of interest, 20 Hz, is inserted into well-known Fast Fourier Transform and bandpass equations in a manner to produce the desired emphasis and deemphasis of information appearing at different frequencies. The frequency figure determines the Fourier transform operation and determines the width of a Hanning window used in the operation.

Again, the one-dimensional processes of blocks 108 and 110 are preferably performed transversely with the orientation of the parallel lines 72 in the image.

The image is then thresholded as shown in block 114 to produce a binary, black and white image consisting only of digital representations of the locations of parallel lines 72, in which dark pixels containing no parallel lines 72 are represented by 0 hexadecimal (h) and "lit" pixels at the location of a parallel line 72 are represented by a −1 h. Thus, if eight digital bits are provided to represent each pixel, dark pixels will be represented by 00h and lit pixels by FFh. The thresholded image is then one-dimensionally skeletonized in block 116. In skeletonizing, the width of each line, which may encompass a plurality of pixels, is examined transversely and the pixels "lit" across the width of the line are darkened except for a single pixel located at the center of the line's width. Thus, a line that is several pixels wide is transformed into a line that is a single pixel in width.

As shown in block 118, the entire length of each line in the area of interest is traversed by doing a pixel-by-pixel constrained search to locate the next lit pixel and, when a lit pixel is located, to then carefully associate the found pixel with one of the lines that are being detected. Where breaks in the lines occur, the disjoint pieces of the line are identified and the slope of the line at each end of the break is examined. Data for the position of the line in the broken area is then generated by interpolation according to the slopes at the ends of the disjoint line segments.

The line detection algorithm is then complete, in that a single-pixel width binary image of the parallel lines 72 has been generated and any discontinuous portions of the parallel lines 72 have been associated with the other portions of the same line. As noted before, the deviation of the parallel lines 72 from straightness is related to the topography of the optic nerve head at the point of deviation, and the topography can be calculated from the deviations and breaks in the parallel lines 72.

Figure 8:
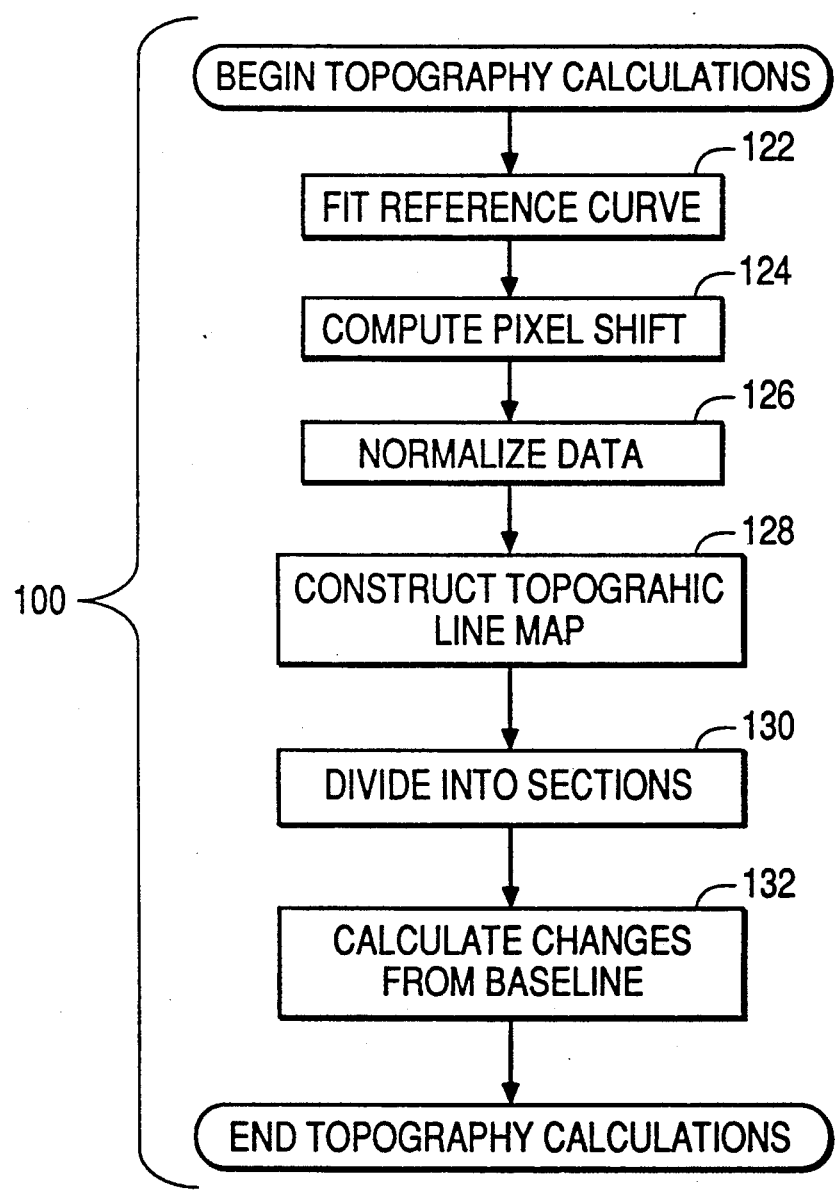
FIG. 8 is a flowchart showing the topography calculation algorithms of the present invention.
Figure 9:
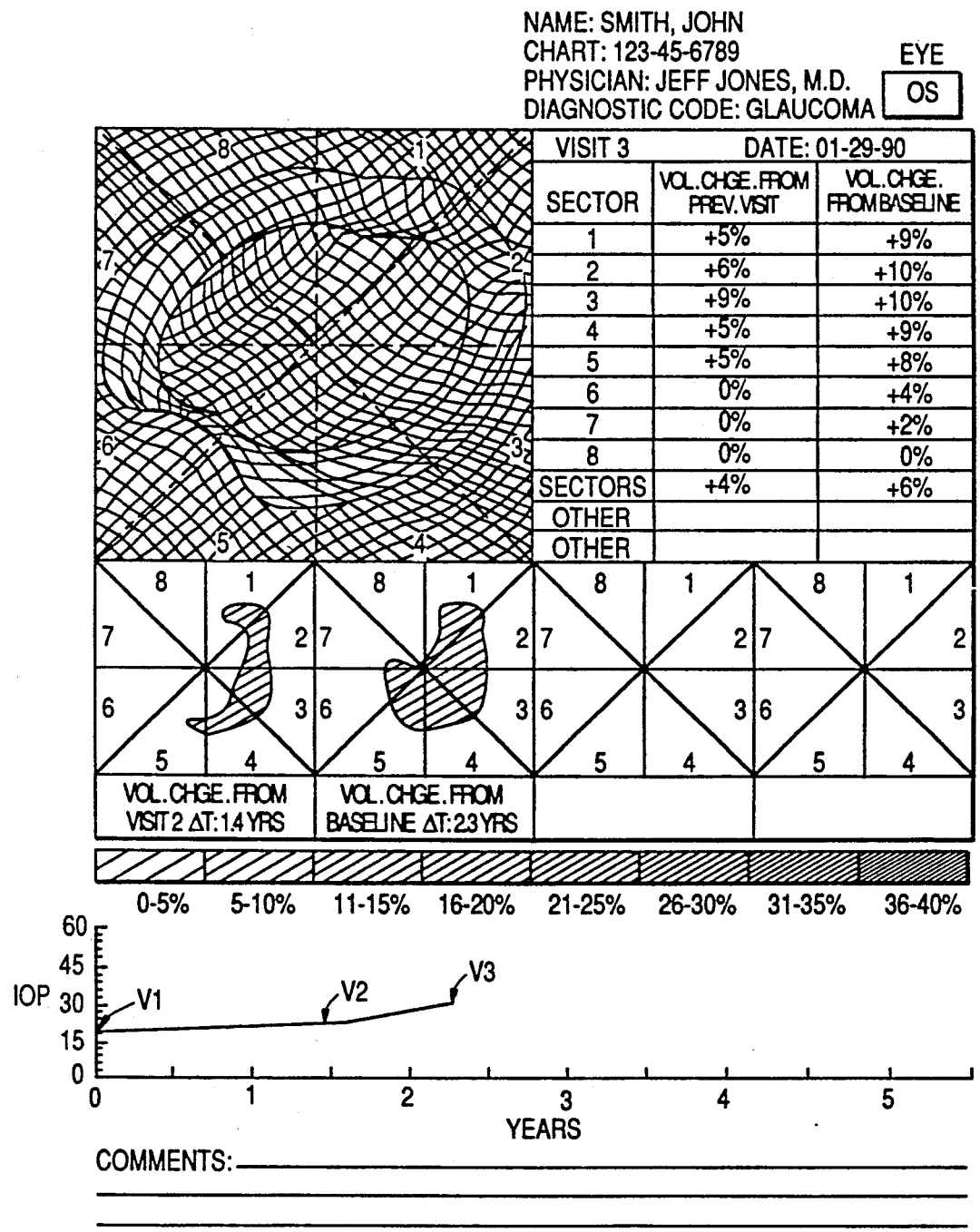
FIG. 9 is an ocular structural analysis report according to the present invention.

When the line traversing process has been completed satisfactorily, then topography calculations are performed as shown in block 100 of FIG. 6. Referring now to FIG. 8, a flowchart of the topography calculations of block 100 in FIG. 6 is shown. In the first step, block 122, a reference curve is fit to the line data to determine the effect of the optics of eye 46 on the projection of parallel lines 72. The reference curve is fit based on the curvature of lines located on the retina 52 away from optic nerve head 50, which are generally less affected by topographical variations. The reference curvature identified, along with the interline spacing, which may be varied by the optics of eye 46, is used to determine how the optics of eye 46 changed the image that was captured. Since it is known that a straight line was projected onto the retina 52, it is also known that all of the curvature measured in the reference curve was introduced by the optics of the eye. In addition, the spacing of the lines as projected is known, so that any variations in the line spacing observed can also be ascribed to the optics of the eye. As will be explained, the reference curvature identified is taken out of the line data to correct the line data so as to obtain absolute measurements. The normalized line data can be used for comparison to data obtained in subsequent and previous follow-up examinations. Such normalization is necessary since the optics of the eye 48 may change between examinations. Variation in the images of optic nerve head 50 resulting from changes in the patient's eyesight would appear as a change in the topography of optic nerve head 50. Thus, even if the optic nerve head 50 has not changed, a false change in the topography of the optic nerve head 50 might be detected due merely to changes in the patient's eyesight over the course of several years.

In block 124, the pixel shift that is produced by the eye's optics is compute reference curve and from the changes in interline spacing to compensate for the optics of the eye 46. Then, in block 126, the data is normalized by translation into a new coordinate system taking into account the pixel shift calculated in block 124. The new coordinate system will be located based on the user defined area and major landmark selected. Although less preferred, the pixel shift could also be calculated relative to endpoints of each of the lines, thus eliminated the curve fitting process of block 122. Since the optics of the cornea 48 of eye 46 alter the interline spacing, this normalization algorithm corrects the data back to a standard reference of known interline spacing.

As shown in block 128, a topographic map is then constructed showing the depth and volume of the defined area of interest which, for glaucoma detection and treatment, preferably includes the optic nerve head 50. The topographic map is constructed using the information of the skeletonized contour lines that were identified as described above. The information from each of the two or more images captured, one having vertical parallel lines 72 and one having horizontal parallel lines 72, is combined to form a single topographic map with contour lines along both X and Y axes. The data from each of the images that is used to form the topographic map is registered with other data using the landmarks identified by the operator or by the system to compensate for any movement of the eye 46 between the sequential image capture operations.

The user defined area is then divided into sections in block 130 to maximize sensitivity to change in depth of a specified region over time. The sections are preferably eight half-quadrants, each comprising a section of 45 degrees of arc extending from the center of the area of interest that is being analyzed. As noted previously, once the topographic map has been created, it is desirable to store data representing the topographic map generated and identifying the landmarks selected in the permanent storage record associated with the image. Of course, any of a number of other methods of sectioning the user defined area could also be used, producing any of a number of geometrically shaped areas. For example, concentric ring-shaped areas or adjacent rectangular sections could be provided. The quadrant method described first is preferred since it can be easily visualized by medical personnel discussing the results, independently of viewing the report produced by the apparatus of the present invention. For example, a doctor may refer to changes in the lower portion of the upper right quadrant of an optic nerve head 50, and the location of this change can be understood and visualized by other persons without reference to section numbers identified on the report.

In block 132, changes in the volume of optic nerve head 50 over time are calculated by comparing the topographical maps calculated on previous occasions with the latest topographical map produced by correlation of the two or more images taken. The comparison of block 132 correlates the landmarks in the area of interest between the images to be compared and performs any shift necessary to register or match up the images, and then compares the area under the topographic maps at the corresponding points of the two images to determine any change in volume of the optic nerve. These changes are measured for each section identified in block 130. The volumes are calculated by determining the displacement of lines in one topographical map relative to the lines in another topographical map and integrating to determine the volume difference, if any.

Referring again to FIG. 6, the next step, block 102, is to generate a report on optic structure based on this data. This report is preferably an easy-to-interpret graphical representation of several topographic features of the optic nerve head, such as the sample report shown in FIG. 8. The report shown in FIG. 8 is designed to break up the area of interest into sections allowing more sensitive means of image analysis. The report preferably includes a perspective representation of the optic nerve head along with a topographic map of the data. Two columns of data are provided showing change from baseline and change from previous visits. This data is displayed as a percent change. Total change over the entire optic nerve head 50, the cup if any of the optic nerve head 50 or an operator-defined area could also be represented in the report. It may also be desirable to present tables of actual data rather than presenting only percentage changes. For example, specific depth values may be shown for points on the optic nerve head 50.

The data in the report is also graphically represented with shaded illustrations providing an easy-to-interpret representation of volumetric change in each section as compared to baseline and previous visits. Additionally, the user has a flexible portion of the report in which parameters may be added and then graphically followed over time. One such parameter to be followed over time which is illustrated in the report of FIG. 8 is intraocular pressure (IOP). The individual reviewing the report can review any changes in IOP over time and compare these IOP readings with variations in optic nerve head topography. Another parameter that may be followed over time, which is not shown in the sample report, is a visual field index measured using a perimeter as described previously in the background section. In conclusion, this report is a unique and valuable graphical representation of the data in which copyright is claimed by the assignee of this patent.

Figure 10:
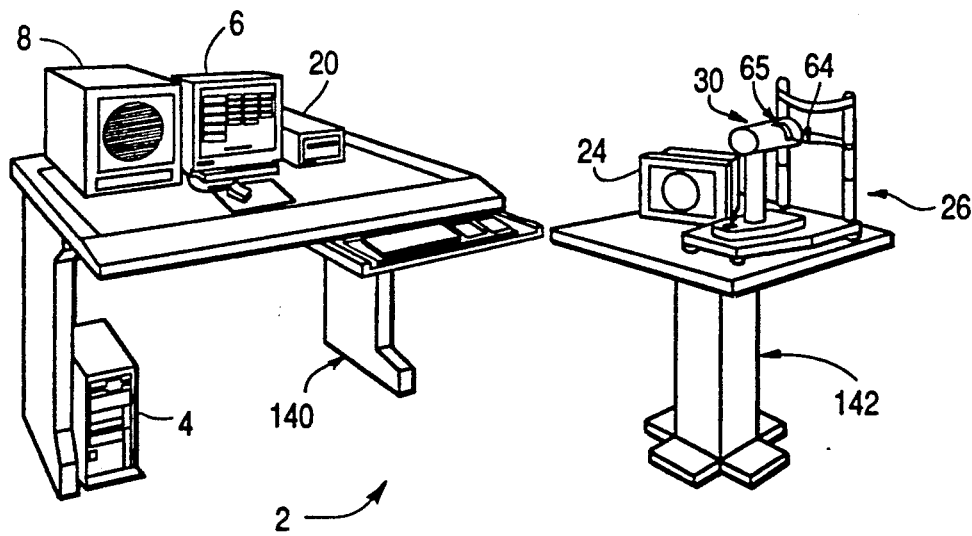
FIG. 10 is a perspective view of the inventive apparatus organized as a clinical workstation.

In FIG. 10, the apparatus 2 of the present invention is shown arranged for clinical use. The personal computer 4, image monitor 8, text monitor 6, and large scale storage disk 20 are arranged on a first table 140, while the observation video monitor 24, chin and joystick assembly 26, and the associated housing 30 holding the optical subsystem are located on a second table 142 arranged at right angles to the first table 140.

Thus, the limitations of prior art methods relative to detecting lines that are not sharply focused across the nerve head tissue are overcome by the novel apparatus and method of line detection disclosed herein.

STATEMENT OF INDUSTRIAL APPLICABILITY

The topographical analysis apparatus of the present invention was designed to accurately measure the topography of the retina including the optic nerve head and to generate an easy to interpret report. While the primary use of the product will be for early detection of glaucoma, the instrument could also be used for measuring a variety of retinal topography. In particular, the algorithms disclosed herein for use in diagnosing glaucoma could be applied to other areas of the retina where topographic information provides useful diagnostic information. One such application would be in the detection of cystoid macular edema (CME) without the use of fluorescein angiography. In addition, tumor growth or shrinkage may be tracked using the system. Finally, the apparatus of the system can be used in a multifunctional capacity, for example for fluorescein angiography, color fundus photography, black-and-white fundus photography, or indo-cyanine green angiography in addition to glaucoma diagnosis.

We claim:

1. An apparatus for topographically mapping an internal ocular surface, comprising:

projection means for projecting a plurality of parallel lines onto the internal ocular surface in a specified line orientation and with a specified direction of projection;

camera means for capturing an image of the internal ocular surface having parallel lines projected thereon, the image being captured at an angle from the direction of projection;

digitizing means connected to the camera means for generating digital picture element data representative of the image of the internal ocular surface;

computer means connected to the digitizing means for identifying the picture element locations of images of the parallel lines in the image and for generating a topographical map of said internal ocular surface based on imaged curvatures of the projected parallel lines;

mass storage means associated with the computer means for long-term storage of data, the data stored representing at least one of two data types, the two data types being data representing said topographical map, and said digital picture element data; and comparison means associated with the computer means for retrieving at least one of the types of previously stored data relating to said internal ocular surface and then comparing a first topographical map generated from said previously stored data to a second topographical map generated from more recently obtained data relating to the same internal ocular surface, to identify differences in topography between said first and second maps.

2. The apparatus of claim 1 wherein the projection means and the camera means are contained in a single housing.

3. The apparatus of claim 1 wherein the camera means is a video camera mounted to have a central axis of view of the internal ocular surface, and at least a portion of the projection means is movable relative to said axis of view for selectively projecting the parallel lines from at least two directions relative to said axis of view.

4. The apparatus of claim 3 wherein the computer means uses data gathered from at least two images to form a topographical map, each of the said two images being taken with the parallel lines projected onto the internal ocular surface from a different direction.

5. The apparatus of claim 4 wherein the parallel lines in one of the two images are projected perpendicularly to the parallel lines of the other image.

6. The apparatus of claim 3 wherein the projection means includes a light source, a line grid, and a mirror, mounted for selective rotation about the axis of view.

7. The apparatus of claim 1 wherein the mass storage means is an optical drive capable of storing data relating to a large number of patients.

8. The apparatus of claim 1 wherein the comparison means divides the topographical maps being compared into defined regions and calculates differences between the topographical maps according to the defined regions.

9. The apparatus of claim 1 further including display means connected to the computer means for producing a report, said report providing information on topographical differences identified by the comparison means.

10. The apparatus of claim 9 wherein the report further includes information on patient intraocular pressures recorded in each case at about the times of capture of the image data used by the comparison means to identify topographical differences.

11. The apparatus of claim 9 wherein the report further includes information on patient visual fields recorded in each case at about the times of the capture of the image data used by the comparison means to identify topographical differences.

12. The apparatus of claim 1 wherein the computer means uses at least one one-dimensional processing algorithm to identify the picture element locations of images of the parallel lines.

13. The apparatus of claim 12 wherein at least one one-dimensional processing algorithm is executed transversely to the orientation in the image of the projected parallel lines.

14. The apparatus of claim 12 wherein one one-dimensional processing algorithm is a Fourier transform algorithm.

15. The apparatus of claim 12 wherein one one-dimensional processing algorithm bandpass filter algorithm.

16. The apparatus of claim 12 wherein one one-dimensional processing algorithm is a line skeletonizing algorithm.

17. The apparatus of claim 12 wherein the computer uses a multiple step algorithm made up of individual algorithms to identify the picture element locations of images of the parallel lines, with said individual algorithms including Fourier transform, bandpass filter, and skeletonizing algorithms.

18. The apparatus of claim 17 wherein the individual algorithms further include a dilation algorithm, a thresholding algorithm and erode and restore algorithms.

19. The apparatus of claim 12 wherein the computer uses a multiple step algorithm made up of individual algorithms to identify the picture element locations of images of the parallel lines, with said individual algorithms including a line traversal algorithm for performing a pixel-by-pixel constrained search to connect associated line segments.

20. The apparatus of claim 1 wherein the comparison means provides as an output a quantitative topographical comparison.

21. The apparatus of claim 20 wherein part of the output quantitative comparison is an indication of the amount of relative increase or decrease in the volume of an optic nerve head.

22. The apparatus of claim 1 further including infrared filter means associated with the camera means for reducing the amount of infrared energy reaching the camera means.

23. The apparatus of claim 1 wherein the projection means comprises an infrared illumination device for projecting lines of infrared energy on the internal ocular surface.

24. The apparatus of claim 1 wherein the projection means selectively projects the lines during a first type of time period when an image is being captured by the apparatus and does not project lines during a second type of time period when an image is not being captured.

25. The apparatus of claim 1 adapted to further perform in addition to the functions defined at least one of the functions of black-and-white fundus photography, color fundus photography, fluorescein angiography, and indo-cyanine green angiography.

26. A device for collecting image data describing an internal ocular surface, comprising:
unitary housing means for locating image data collection equipment, including a forward surface adapted to be brought into proximity with a frontal surface of a patient's eye, the forward surface shaped to prevent contact of the forward surface with the frontal surface of the eye, and the forward surface having associated with it aperture means for passing light from either side of the forward surface to the other;
camera means associated with the housing means for collecting image data, the camera means located to the rear of the forward surface and having a field of view including a view axis between the camera means and the eye, with the view axis passing through the aperture means;
projection means associated with the housing means for projecting radiation energy onto the internal ocular surface, the projection means including a radiation source means for producing radiation and a reflecting means for reflecting radiation, the reflecting means located on a separate projection axis proximate to the view axis between the camera means and the forward surface of the housing means, wherein the projection means projects a plurality of parallel radiative energy lines onto the internal ocular surface.

27. The device of claim 26 wherein the radiation source means and the reflecting means are rotatable relative to the view axis to permit projection of lines onto the ocular surface from different directions relative to the view axis.

28. The device of claim 27, wherein the housing means is a substantially cylindrical housing enclosing the projection means and the camera means.

29. A device for collecting image data describing an internal ocular surface, comprising:
   unitary housing means for locating image data collection equipment, including a forward surface adapted to be brought into proximity with a frontal surface of a patient's eye, the forward surface shaped to prevent contact of the forward surface with the frontal surface of the eye, and the forward surface having associated with it aperture means for passing light from either side of the forward surface to the other;
   camera means associated with the housing means for collecting image data, the camera means located to the rear of the forward surface and having a field of view including a view axis between the camera means and the eye, with the view axis passing through the aperture means;
   projection means associated with the housing means for projecting radiation energy onto the internal ocular surface, the projection means including a radiation source means for producing radiation and a reflecting means for reflecting radiation, the reflecting means located on a separate projection axis proximate to the view axis between the camera means and the forward surface of the housing means;
   wherein the radiation source means and the reflecting means are located in a line substantially perpendicular to the view axis and wherein the radiation source means and the reflecting means are rotatable relative to the view axis to permit projection of lines onto the ocular surface from different directions relative to the view axis.

30. A device for collecting image data describing an internal ocular surface, comprising:
   unitary housing means for locating image data collection equipment, including a forward surface adapted to b brought into proximity with a frontal surface of a patient's eye, the forward surface shaped to prevent contact of the forward surface with the frontal surface of the y, and the forward surface having associated with it aperture means for passing light from either side of the forward surface to the other;
   camera means associated with the housing means for collecting image data, the camera means located to the rear of the forward surface and having a field of view including a view axis between the camera means and the eye, with the view axis passing through the aperture means;
   projection means associated with the housing means for projecting radiation energy onto the internal ocular surface, the projection means including a radiation source means for producing radiation and a reflecting means for reflecting radiation, the reflecting means located on a separate projection axis proximate to the view axis between the camera means and the forward surface of the housing means, wherein the projection means comprises an infrared illumination device for projecting lines of infrared energy on the internal ocular surface.

31. A device for collecting image data describing an internal ocular surface, comprising:
   unitary housing means for locating image data collection equipment, including a forward surface adapted to be brought into proximity with a frontal surface of a patient's eye, the forward surface shaped to prevent contact of the forward surface with the frontal surface of the eye, and the forward surface having associated with it aperture means for passing light from either side of the forward surface to the other;
   camera means associated with the housing means for collecting image data, the camera means located to the rear of the forward surface and having a field of view including a view axis between the camera means and the eye, with the view axis passing through the aperture means;
   projection means associated with the housing means for projecting radiation energy onto the internal ocular surface, the projection means including a radiation source means for producing radiation lines and a reflecting means for reflecting radiation, the reflecting means located on a separate projection axis proximate to the view axis between the camera means and the forward surface of the housing means;
   wherein the projection means selectively projects the lines during a first type of time period when an image is being captured by the apparatus and does not project lines during a second type of time period when an image is not being captured.

32. The apparatus of claim 1 adapted to further perform in addition to the functions defined at least one of the functions of black-and-white fundus photography, color fundus photography, fluorescein angiography, and indo-cyanine green angiography.

33. A method for automatically identifying changes in internal ocular topography, comprising the steps of:
   obtaining a first set of digital data representing an image of an area of interest using an apparatus, said apparatus projecting parallel lines on the area of interest through an ocular cornea and detecting the reflected image of the lines from the area of interest, the angle of detection being different than the angle of line projection;
   obtaining a second set of digital data representing an image of the area at a later time using an apparatus, said apparatus projecting parallel lines on the area of interest through the cornea and detecting the reflected image of the lines from the area of interest, the angle of detection being different than the angle of line projection;
   producing a first set of line data in a computer identifying locations of images of the parallel lines, by executing at least one one-dimensional data filtering algorithm on the first set of data;
   producing a second set of line data in the computer identifying locations of images of the parallel lines, by executing at least on one-dimensional data filtering algorithm on the second set of data;
   normalizing the first set of line data as required to compensate for ocular imaging effects;
   normalizing the second set of line data as required to compensate for ocular imaging effects;

generating a topographical map in the computer for the first set of data based on imaged curvatures of the projected parallel lines;

generating a topographical map in the computer for the second set of data based on imaged curvatures of the projected lines;

electronically comparing the topographical maps for the first and second sets of data to quantitatively identify changes in volume of the area of interest between the time of obtaining the first set of digital data and the time of obtaining the second set of digital data.

34. The method of claim 33 wherein the steps of producing line data each include application of a Fourier transform algorithm.

35. The method of claim 33 wherein in the steps of producing line data, at least one one-dimensional processing algorithm is executed transversely to the orientation in the image of the projected lines.

36. The method of claim 33 wherein the steps of producing line data each include application of a bandpass data filtering algorithm.

37. The method of claim 33 wherein the steps of producing line data each include application of a line skeletonizing algorithm.

38. The method of claim 33 wherein the steps of producing line data each include application of a multiple step algorithm made up of individual algorithms for identifying the picture element locations of images of the parallel lines, with said individual algorithms including Fourier transform, bandpass filter, and skeletonizing algorithms.

39. The method of claim 38 wherein the individual algorithms further include a dilation algorithm, a thresholding algorithm and erode and restore algorithms.

40. The method of claim 33 wherein the steps of producing line data each include application of a multiple step algorithm made up of individual algorithms for identifying the picture element locations of images of the parallel lines, with said individual algorithms including a line traversal algorithm for performing a pixel-by-pixel constrained search to connect associated line segments.

41. A method for automatically identifying changes in internal ocular topography, comprising the steps of:

obtaining a first set of digital data representing an image of an area of interest using an apparatus, said apparatus projecting parallel lines on the area of interest through an ocular cornea and detecting the reflected image of the lines from the area of interest, the angle of detection being different than the angle of line projection;

obtaining a second set of digital data representing an image of the area at a later time, using an apparatus, said apparatus projecting parallel lines on the area of interest through the cornea and detecting the reflected image of the lines from the area of interest, the angle of detection being different than the angle of line projection;

producing a first set of line data in a computer identifying locations of images of the parallel lines, by executing at least on one-dimensional data filtering algorithm on the first set of data;

producing a second set of line data in the computer identifying locations of images of the parallel lines, by executing at least one one-dimensional data filtering algorithm on the second set of data;

normalizing the first set of line data as required to compensate for ocular imaging effects;

normalizing the second set of line data as required to compensate for ocular imaging effects;

generating a topographical map in the computer for the first set of data based on imaged curvatures of the projected parallel lines;

generating a topographical map in the computer for the second set of data based on imaged ed curvatures of the projected parallel lines;

identifying at least two registration points, one each in the first and second topographical maps, the registration points representing the same physical location in the area of interest;

calculating an offset between registration points in the first and second topographical maps;

electronically comparing the topographical maps for the first and second sets of data to quantitatively identify changes in volume of the area of interest between the tim of obtaining the first set of digital data and the time of obtaining the second set of digital data, taking into account the calculated offset so that points in the first topographical map are compared to corresponding points in the second topographical map.

42. The method of claim 41 wherein the steps of producing line data each include application of a Fourier transform algorithm.

43. The method of claim 41 wherein in the steps of producing line data, at least one one-dimensional processing algorithm is executed transversely to the orientation in the image of the projected lines.

44. The method of claim 41 wherein the steps of producing line data each include application of a bandpass data filtering algorithm.

45. The method of claim 41 wherein the steps of producing line data each include application of a line skeletonizing algorithm.

46. The method of claim 41 wherein the steps of producing line data each include application of a multiple step algorithm made up of individual algorithms for identifying the picture element locations of images of the parallel lines, with said individual algorithms including Fourier transform, bandpass filter, and skeletonizing algorithms.

47. The method of claim 46 wherein the individual algorithms further include a dilation algorithm, a thresholding algorithm and erode and restore algorithms.

48. The method of claim 41 wherein the steps of producing line data each include application of a multiple step algorithm made up of individual algorithms for identifying the picture element locations of images of the parallel lines, with said individual algorithms including a line traversal algorithm for performing a pixel-by-pixel constrained search to connect associated line segments.

* * * * *